United States Patent [19]

Horne, Jr.

[11] 3,950,530

[45] Apr. 13, 1976

[54] PYRROLIDINE INSECT CONTROL AGENTS

[75] Inventor: Charles A. Horne, Jr., Modesto, Calif.

[73] Assignee: Shell Oil Company, Houston, Tex.

[22] Filed: Feb. 9, 1973

[21] Appl. No.: 331,157

Related U.S. Application Data

[63] Continuation-in-part of Ser. No. 250,304, May 4, 1972, abandoned.

[52] U.S. Cl............................ 424/274; 424/DIG. 8
[51] Int. Cl.$^2$........................................... A01N 9/22
[58] Field of Search........................ 424/274, DIG. 8

[56] References Cited
UNITED STATES PATENTS 3,560,523  2/1971  Etienne et al..................... 260/326.9
3,681,339  8/1972  Tetenbaum........................ 260/239

FOREIGN PATENTS OR APPLICATIONS 1,236,842  6/1969  United Kingdom

OTHER PUBLICATIONS

Glushkov et al., Chem. Abst., Vol. 55, p. 7430f (1961).

Primary Examiner—Sam Rosen
Assistant Examiner—Allen J. Robinson

[57] ABSTRACT

2-(Nitromethylene)pyrrolidines are useful for controlling lepidopterous larvae on plants.

4 Claims, No Drawings

PYRROLIDINE INSECT CONTROL AGENTS

This application is a continuation-in-part of copending application, Ser. No. 250,304, filed May 4, 1972, now abandoned.

FIELD OF THE INVENTION

This invention relates to the use of 2-(nitromethylene)pyrrolidines for controlling lepidopterous larvae, and to formulations of such pyrrolidines suitable for that purpose.

SUMMARY OF THE INVENTION

It has now been found that certain pyrrolidines containing a nitromethylene moiety bonded to the ring carbon atom alpha to the ring nitrogen atom are effective killers of certain economically important species of lepidopterous larvae which feed upon the foliage and/or fruit of plants.

DESCRIPTION OF THE PREFERRED EMBODIMENTS

The present invention provides a method for controlling lepidopterous larvae, employing compounds of the formula:

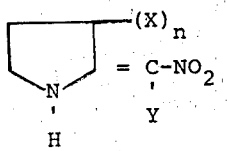

wherein $n$ is 0 or 1, X is methyl, and Y is hydrogen or bromine.

Because of their effects on larvae, one preferred sub-class of this genus is constituted by those species wherein $n = 0$. Highest activity in this sub-class appears to be associated with that species wherein $Y = H$, that is, 2-(nitromethylene)pyrrolidine.

The invention is illustrated in specific cases by the working examples included hereinafter, which describe the preparation and testing, with respect to certain larvae, of typical species of the larvicides of the invention.

The manner in which these larvicides can be prepared is illustrated in the following examples of the preparation of particular species thereof. In all cases, the identity of the product was confirmed by elemental and spectral analyses.

EXAMPLE I: 2-(nitromethylene)pyrrolidine

This compound was prepared as an orange-yellow solid, m.p. 105°–107°, by the process described in Example I, U.S. Pat. No. 3,560,523.

EXAMPLE II: 2-(bromonitromethylene)pyrrolidine 4.0 grams (0.025 mole) of bromine was added dropwise to a stirred solution of 3.2 grams (0.025 mole) of 2-(nitromethylene)pyrrolidine in 50 millilieters of water at 0°C. The precipitate which formed was filtered to give 1.8 grams of a cream-colored powder, melting point: 149°–150.5°C (with decomposition). Cooling the filtrate gave another 0.3 grams. 0.8 grams of the first crop was recrystallized from ethanol to give 0.7 grams of 2-(bromonitromethylene)pyrrolidine as pale yellow needles, melting point: 158°–9°(with decomposition).

EXAMPLE III: 3-methyl-2-(nitromethylene)pyrrolidine

The ethyl imidate of 3-methyl-2-pyrrolidone was prepared from the known 3-methyl-2-pyrrolidone by the method disclosed in British patent 1,236,842.

A solution of 12.7 grams (0.10 mole) of the ethyl imidate of 3-methyl-2-pyrrolidone in 30 milliliters of nitromethane was refluxed for four days with occasional distillation of ethanol by-product to bring the reflux temperature back to 100°C. Excess nitromethane (and ethanol present) then was evaporated under reduced pressure to give a dark oily residue. The residue was dissolved in ethyl acetate and passed through a Florisil column. Evaporation of the solvent from the filtrate left a crystalline residue, which when recrystallized from ether, gave 4.6 grams of 3-methyl-2-(nitromethylene)pyrrolidine, as a white solid, melting point: 47–47.5°C.

These compounds can exist in the forms of two geometric isomers, depending upon the positioning of the substituents on the double bond of the nitromethylene/ring carbon structure, i.e., as cis-trans isomers.

It has been found that the 2-(nitromethylene)pyrrolidines are particularly effective against certain species of lepidopterous larvae (that is, larvae of insects of the order Lepidoptera) that are economically important, in that they feed upon the foliage and fruit of such plants as tobacco, cotton, corn, tomatoes and peppers. In particular, these compounds control such larvae as those of the genus Heliothis, such as *Heliothis zea* (corn earworm; cotton bollworm; tomato fruitworm) and *Heliothis virescens* (tobacco budworm) and the genus Agrotis, such as *Agrotis ipsilon* (black cutworm).

At least one species of these pyrrolidines has been found to have systemic activity — that is, when applied to the roots of a plant, the chemical passes upwards in the plant and affects insects feeding upon juices of the plant, or upon the foliage of the plant. These pyrrolidines exhibit little or no phytotoxicity and are essentially innocuous to plants at dosages which effectively control larvae feeding on the plants. It is believed that these pyrrolidines are absorbed into the plant when placed upon the foliage of the plant.

These pyrrolidines are characterized by low toxicity to animals other than insects, so that they are relatively safe to use and have a minimal effect upon the environment in which they are used. Further, they tend to be unstable to sunlight, so that they have short persistence, thus minimizing any possibly adverse effect that they might have upon the ecology of the environment in which they are used.

The larvicides of this invention can be used to control insects by means, techniques and practices which are conventional in the insecticide art, which are described, for example, in U.S. Pat. No. 3,116,201. For example, the active compound can be either sprayed or otherwise applied in the form of a solution or dispersion, or can be absorbed on an inert finely-divided solid and applied as a dust. Useful solutions for application by spraying, brushing, dipping and the like, can be prepared by using as the solvent any of the well known inert horticultural carriers, including neutral hydrocarbons, such as kerosene and other light mineral oil distillates of intermediate viscosity and volatility. Adjuvants such as spreading or wetting agents can also be included in the solution. These solutions may be employed as such, or more preferably, they can be dispersed or emulsified in water and the resulting aqueous dispersion or emulsion applied as a spray. Solid carrier materials which can be employed include talc, bentonite, lime, gypsum, and similar inert solid diluents. If desired, the active compound can be employed as an aerosol as by dispersing the same into the atmosphere by means of a compressed gas.

The concentration of the active compound to be used with the above carriers is dependent upon many factors, including the carrier employed, the method and conditions of application, and the insect species to be controlled, a proper consideration and resolution of these factors being within the skill of these versed in the insecticide art. In general, however, the compound is effective in concentrations as little as about 0.01% to 0.5% based upon the total weight of the composition, even though under some circumstances as little as about 0.001% or as much as about 2% or even more of the compound can be employed with good results from the worm control standpoint. Concentrates suitable for sale for dilution in the field and/or for ultra-low volume spray applications may contain as much as 25–50% by weight or even more of the insecticide.

The active compound of this invention can be used either as the sole toxic ingredient of the control composition or it can be employed in conjunction with other insecticidally active materials. Representative insecticides of this class include the naturally occurring insecticides such as pyrethrum, rotenone, sabadilla, and the like, as well as the various synthetic insecticides including benzene hexachloride, thiodiphenylamine, cyanides, tetraethyl pyrophosphate, diethyl p-nitrophenyl thiophosphate, dimethyl 2,2-dichlorovinyl phosphate, 1,2-dibromo-2,2-dichloroethyl dimethyl phosphate, azobenzene, and the various compounds of arsenic, lead and/or fluorine.

The effectiveness of the 2-(nitromethylene)pyrrolidines for controlling larvae is illustrated in the following Examples.

EXAMPLE IV

Activity was determined by means of appropriate tests which established the LC$_{50}$ dosage (dosage in grams of test compound per 100 milliliters of solvent required in the solution or suspension used as a spray to kill 50% of the test larvae), of 2-(nitromethylene)pyrrolidines with respect to larvae of several species of insects. The liquid carrier used to prepare the solution or suspension was composed of 2 parts by volume of acetone, 8 parts by volume of water and 0.05 part by volume of Atlox, a wetting agent. The results are summarized in Table I.

TABLE I

| Compound of Example No. | LC$_{50}$ Dosage of Test Compound for Indicated Insect (% Actual Toxicant) | |
| --- | --- | --- |
| | Corn Earworm | Black Cutworm |
| I | 0.0142 | 0.015 |

TABLE I-continued

| Compound of Example No. | LC$_{50}$ Dosage of Test Compound for Indicated Insect (% Actual Toxicant) | |
| --- | --- | --- |
| | Corn Earworm | Black Cutworm |
| II | 0.035 | 0.012 |
| III | 0.025 | 0.008 |

EXAMPLE V

Systemic activity was checked by immersing the roots of broad bean plants (*Vicia faba*) in aqueous solutions containing the test materials at various concentrations, then placing 3rd-instar larvae of the corn earworm on the foliage and noting the mortality of the larvae 48 hours later. The results of the tests are reported in terms of the concentration of test material in the solution required to kill 50% of the larvae. The results are reported in Table II.

TABLE II

| Compound | LC$_{50}$* |
| --- | --- |
| I | 25 |

*parts per million of test compound in the test solution.

What is claimed is:

1. A method for killing lepidopterous larvae of the genus Heliothis or the genus Agrotis upon the foliage or fruit of living plants which comprises applying to the living plant infested with said larvae an effective amount to kill said larvae of a compound of the formula

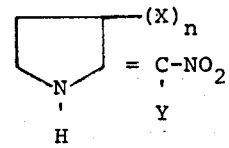

wherein $n$ is 0 or 1, X is methyl and Y is hydrogen or bromine.

2. A method according to claim 1 wherein $n = 0$.
3. A method according to claim 1 wherein Y = H.
4. A method for killing lepidopterous larvae of the genus Heliothis or the genus Agrotis upon the foliage or fruit of living plants which comprises applying to the living plant infested with said larvae an effective amount to kill said larvae of a composition comprising from about 0.01 to about 2 percent by weight of the composition of a compound of the formula

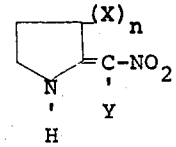

wherein $n$ is 0 or 1, X is methyl and Y is hydrogen or bromine, and liquid or pulverulent solid horticultural carrier therefor.

* * * * *